US010051787B2

(12) United States Patent
Todd et al.

(10) Patent No.: US 10,051,787 B2
(45) Date of Patent: Aug. 21, 2018

(54) HARVESTING HEAD WITH YIELD MONITOR

(71) Applicant: Deere & Company, Moline, IL (US)

(72) Inventors: William D. Todd, Bettendorf, IA (US); Bhanu Kiran Palla, Bettendorf, IA (US)

(73) Assignee: Deere & Company, Moline, IL (US)

( * ) Notice: Subject to any disclaimer, the term of this patent is extended or adjusted under 35 U.S.C. 154(b) by 135 days.

(21) Appl. No.: 15/156,731

(22) Filed: May 17, 2016

(65) Prior Publication Data

US 2017/0332551 A1 Nov. 23, 2017

(51) Int. Cl.
*A01D 41/127* (2006.01)
*A01D 57/01* (2006.01)
*A01D 41/06* (2006.01)
*G01N 33/02* (2006.01)
*A01D 101/00* (2006.01)

(52) U.S. Cl.
CPC ........... *A01D 41/127* (2013.01); *A01D 41/06* (2013.01); *A01D 57/01* (2013.01); *G01N 33/025* (2013.01); *A01D 2101/00* (2013.01)

(58) Field of Classification Search
CPC .. A01D 41/06; A01D 41/127; A01D 41/1271; A01D 41/1272; A01D 45/02; A01D 45/021; A01D 57/01; A01D 2101/00; G01N 33/025
See application file for complete search history.

(56) References Cited

U.S. PATENT DOCUMENTS

| 5,970,800 A * | 10/1999 | Gunneskov | G01F 1/66 73/861.28 |
|---|---|---|---|
| 9,578,808 B2 * | 2/2017 | Dybro | A01D 75/00 |
| 9,668,420 B2 * | 6/2017 | Anderson | A01D 75/00 |
| 2003/0004630 A1 * | 1/2003 | Beck | A01D 41/127 701/50 |
| 2014/0230391 A1 * | 8/2014 | Hendrickson | G01N 33/0098 56/10.2 R |
| 2014/0230580 A1 * | 8/2014 | Dybro | A01D 45/021 73/865 |

(Continued)

FOREIGN PATENT DOCUMENTS

| EP | 0843959 A1 | 5/1998 |
| EP | 2944179 A1 | 11/2015 |
| WO | 2013078328 A2 | 5/2013 |

OTHER PUBLICATIONS

European Search Report issued in counterpart application No. 17170396.0 dated Oct. 19, 2017. (7 pages).

*Primary Examiner* — Alicia Torres
*Assistant Examiner* — Adam J Behrens
(74) *Attorney, Agent, or Firm* — Rathe Lindenbaum LLP

(57) ABSTRACT

A harvesting head yield monitor comprises two sensing elements (328, 330) respectively disposed in two adjacent row unit covers (114). A driver circuit (400) drives one of these sensing elements (328) to produce a high radio frequency signal. The other sensing element (330) receives the signal. A signal conditioning circuit (402) receives the signal from the other sensing element. A controller (404) coupled to the signal conditioning circuit converts the received signal into a signal that indicates the crop yield of the row unit that is disposed underneath the two adjacent row unit covers.

12 Claims, 5 Drawing Sheets

(56) References Cited

U.S. PATENT DOCUMENTS

| | | | | |
|---|---|---|---|---|
| 2014/0236381 A1* | 8/2014 | Anderson | ............. | A01D 75/00 |
| | | | | 701/1 |
| 2015/0293029 A1* | 10/2015 | Acheson | ............ | G01N 33/0098 |
| | | | | 356/51 |
| 2015/0327440 A1* | 11/2015 | Dybro | .................... | A01D 75/00 |
| | | | | 73/862.541 |
| 2016/0084813 A1* | 3/2016 | Anderson | ............ | A01D 41/127 |
| | | | | 702/5 |
| 2016/0084987 A1* | 3/2016 | Dybro | .................... | G01V 99/00 |
| | | | | 702/5 |
| 2016/0113199 A1* | 4/2016 | Jongmans | .......... | A01D 41/1273 |
| | | | | 56/10.2 R |
| 2016/0338263 A1* | 11/2016 | Dybro | .................. | A01D 34/008 |
| 2017/0176595 A1* | 6/2017 | McPeek | ................. | G01S 17/89 |

\* cited by examiner

US 10,051,787 B2

HARVESTING HEAD WITH YIELD MONITOR

FIELD OF THE INVENTION

This invention relates generally to agricultural harvesting heads for agricultural combines. More particularly it relates to yield monitors located on harvesting heads. It also relates to sensor arrangements for sensing physical characteristics of ears of corn.

BACKGROUND OF THE INVENTION

In recent years, determining the physical characteristics of crops being harvested during harvesting has become increasingly important. Further, it is also increasingly important to determine these crop characteristics with a higher resolution. In previous years, knowing crop characteristics on a field by field basis was enough. Recently it has become increasingly important to determine crop characteristics on a meter-by-meter, row-by-row, or even plant-by-plant basis.

What is needed, therefore, is an improved arrangement for sensing crop characteristics in an agricultural harvesting head, and more particularly in a corn head.

It is an object of this invention to provide such a system.

SUMMARY OF THE INVENTION

In accordance with a first aspect of the invention, a harvesting head yield monitor for a row unit is provided, wherein the row unit comprises a row unit gearbox, first and second row unit arms coupled to the row unit gearbox and extending forward therefrom, first and second deck plates supported on top of the first and second row unit arms, respectively, and first and second gathering chains disposed on top of the first and second row unit arms, and wherein the yield monitor comprises a first row unit cover disposed above the first gathering chain and the first deck plate, wherein the first row unit cover comprises a first hollow plastic body; a first sensing element disposed inside the first hollow plastic body immediately above the first gathering chain and the first deck plate; a driver circuit electrically coupled to the first sensing element and configured to drive the first sensing element to generate a high-frequency radio signal and; a second row unit cover disposed above the second gathering chain and the second deck plate wherein the second row unit cover comprises a second hollow plastic body; a second sensing element disposed inside the second hollow plastic body immediately above the second gathering chain and the second deck plate; a signal conditioning circuit electrically coupled to the second sensing element and configured to receive the high-frequency radio signal.

The driver circuit may be disposed inside the first hollow plastic body, and the signal conditioning circuit may be disposed inside the second hollow plastic body.

The yield monitor may further comprise a first digital microprocessor-based controller coupled to the driver circuit and having a CAN bus transceiver, and the first digital microprocessor-based controller may be disposed within the first hollow body, and the first digital microprocessor-based controller may be configured to control the driver circuit.

The yield monitor may further comprise a second digital microprocessor controller coupled to the signal conditioning circuit and having a CAN bus transceiver, the second digital microprocessor-based controller may be disposed within the second hollow body, and the second digital microprocessor controller may be configured to receive signals from the signal conditioning circuit.

The first sensing element and the second sensing element may be disposed on opposing lateral sides of a corn ear collection region and during harvesting operation of the harvesting head an accumulation of ears of corn may be interposed between the first sensing element and the second sensing element.

The yield monitor may further comprise a first deck plate that is planar and generally horizontal and is disposed at least partially underneath the first row unit cover and extends toward the second row unit cover, and a second deck plate that is planar and generally horizontal and is disposed at least partially underneath the second row unit cover.

The first deck plate may be disposed at least partially underneath the first sensing element, and the second deck plate may be disposed at least partially underneath the second sensing element.

The first gathering chain may be disposed at least partially underneath the first sensing element, and the second gathering chain may be disposed at least partially underneath the second sensing element.

DETAILED DESCRIPTION OF THE DRAWINGS

Figure 1:
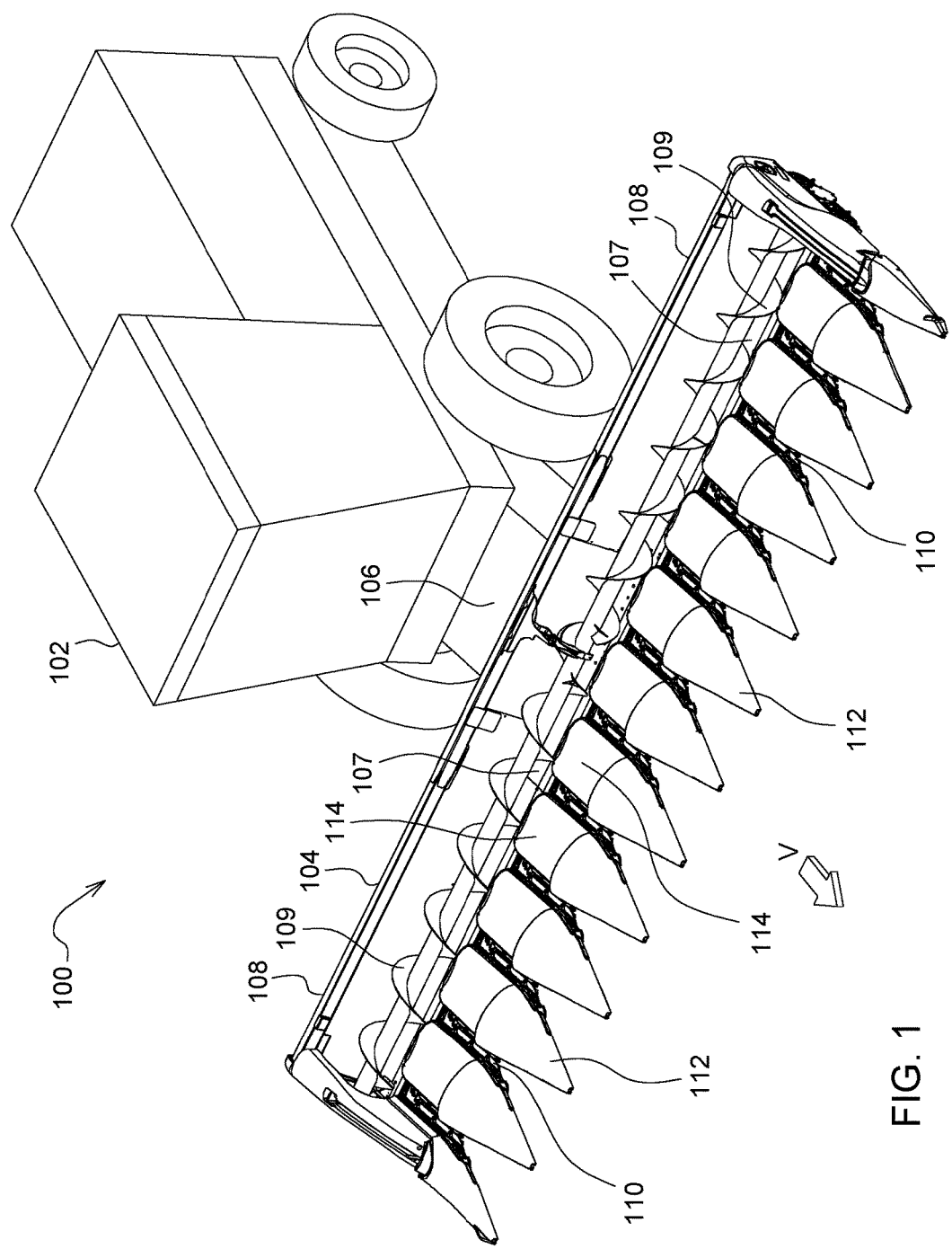
FIG. 1 is a perspective view of an agricultural combine supporting an agricultural harvesting head (a corn head) in accordance with the present invention.
Figure 2:
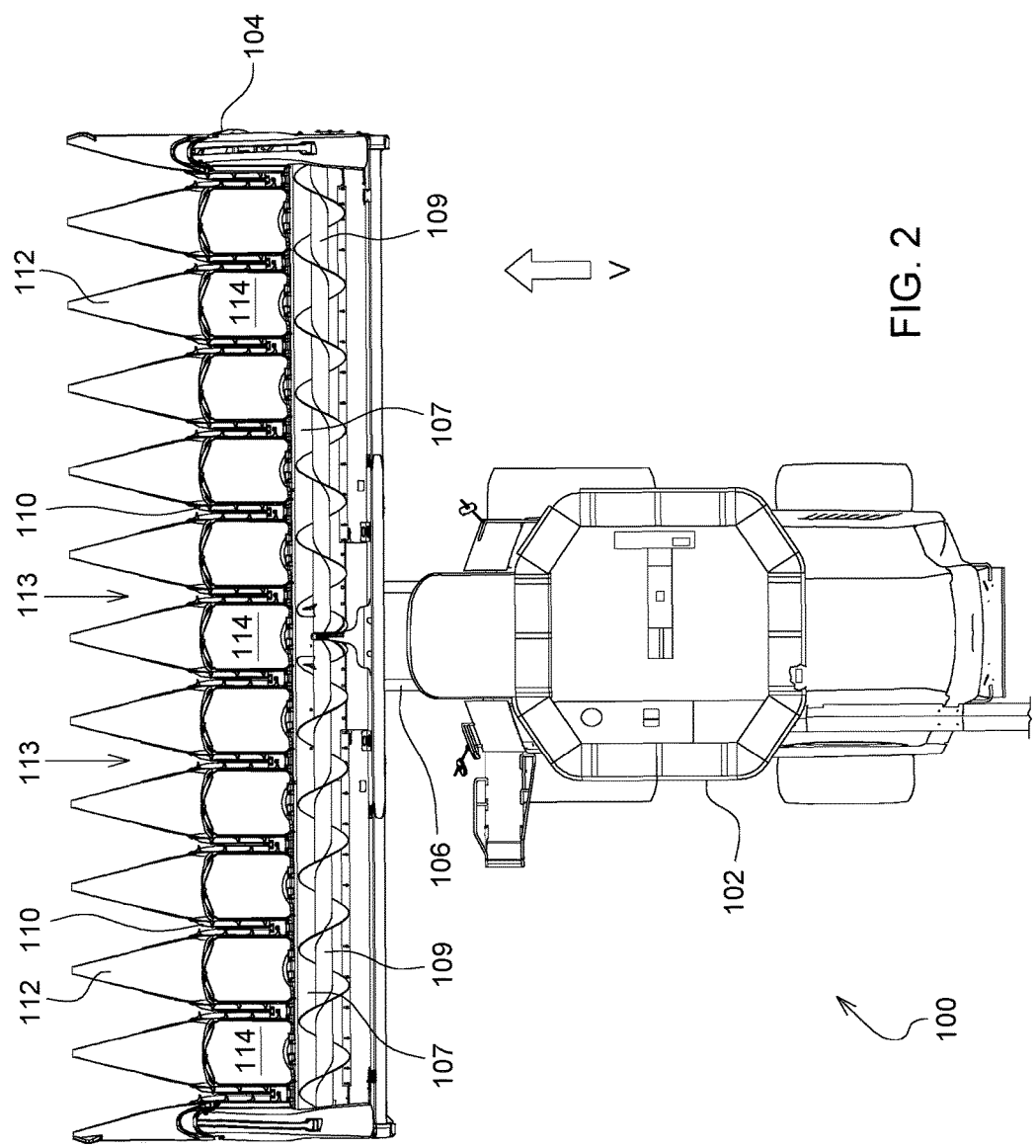
FIG. 2 is a plan view of the agricultural combine of FIG. 1.

In FIG. 1, an agricultural harvester 100 comprises a self-propelled agricultural combine 102 and an agricultural harvesting head 104 supported on the front of the agricultural combine 102. The agricultural harvesting head 104 is supported on a feeder house 106 which is supported on and extends forward from the front of the agricultural combine 102. The agricultural harvester 100 is driven in a direction "V" as it travels through the field harvesting crops.

The agricultural harvesting head 104 includes a frame 108 which extends substantially the entire width of the agricultural harvesting head 104. The frame 108 is elongate and extends laterally, i.e. perpendicular to the direction of travel "V".

The frame 108 supports a plurality of row units 110 (e.g. the 12 shown herein) that are spaced apart laterally and extend across substantially the entire width of the frame 108. The row units 110 function to separate ears of corn from the cornstalks and to convey the ears of corn rearward into an auger 109. The auger 109 conveys the ears of corn into the agricultural combine 102.

The frame 108 also comprises a plurality (e.g. 13) of points 112 or crop dividers. The points 112 are pointed at their forward ends to pass between adjacent rows of crops and push the plant stalks into a narrowing gap 113 formed by each pair of adjacent points. The points are generally triangular in plan view and have a one point facing forward in the direction "V".

The frame 108 supports an auger trough 107 that is horizontal and extends substantially the entire width of the agricultural harvesting head 104. The auger 109 is elongate and is disposed immediately above the auger trough 107 to engage ears of corn and carry them inwardly to a central region of the agricultural harvesting head 104. The auger then pushes the accumulated ears of corn rearward into the feeder house 106, which has an internal conveyor configured to carry the ears of corn upward and into the agricultural combine 102.

The frame 108 also supports a plurality (e.g. 11) of row unit covers 114 that are disposed behind the points 112 and cover the exposed mechanical workings of each row unit 110. The covers 114 prevent plant matter and trash from fouling the row units 110.

The points 112 and the row unit covers 114 are formed of a high density plastic (e.g. polypropylene, polyethylene, nylon). To form the points 112 and the covers 114, plastic pellets are melted in a heated gyrating mold, thus coating all the exposed inside surfaces of the mold and forming a hollow shell with thick plastic walls. This process is called "rotomolding".

The points 112 in the row unit covers 114 are pivotally coupled together at pivot points that extend laterally. The forward ends of the points 112 can be pivoted upward with respect to the covers 114 about the pivot axis defined by the pivot points.

The covers 114 are pivotally coupled to the frame 108. The covers 114 are pivotally coupled at the rear of the covers to pivot about a laterally extending axis. The forward end of each cover 114 can be lifted to expose the mechanical elements workings of each row unit for repair and maintenance.

Figure 3:
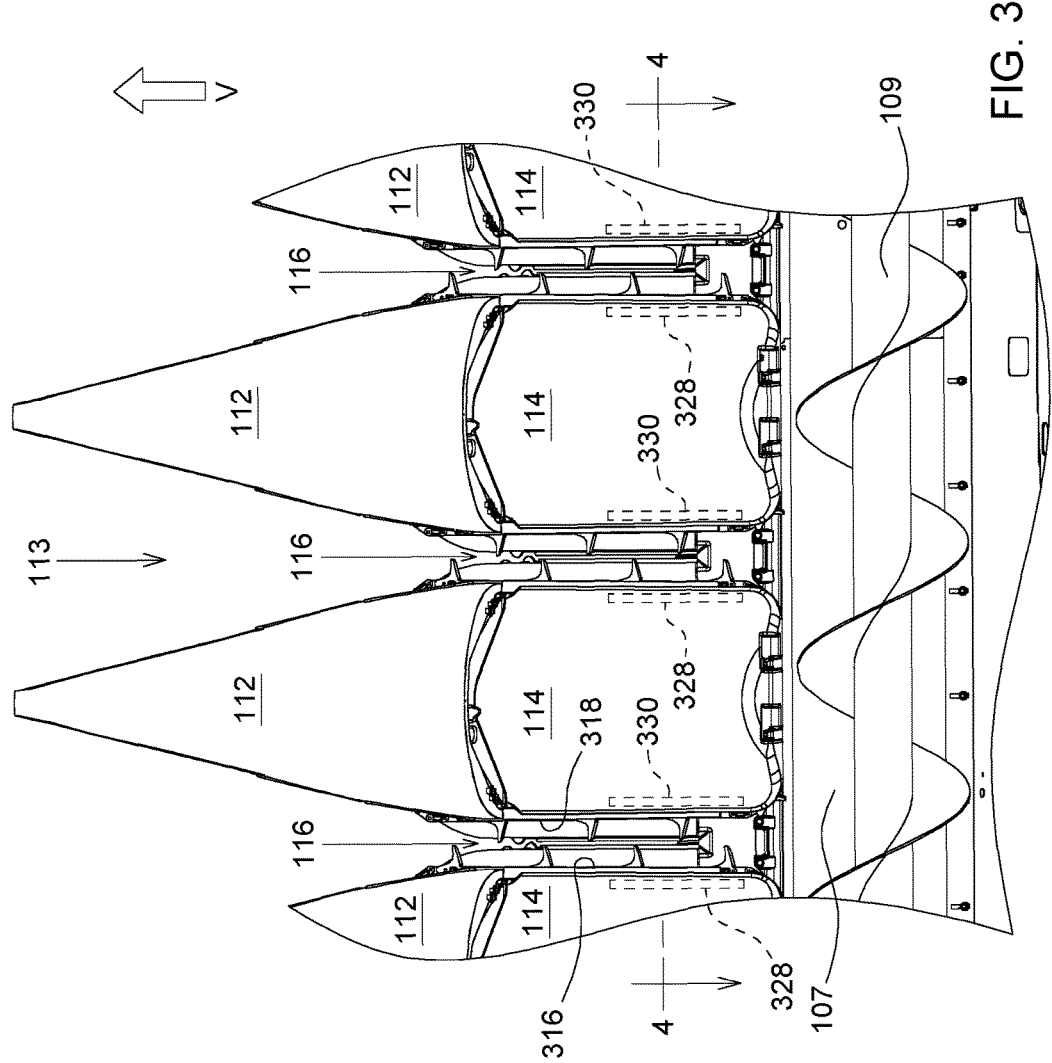
FIG. 3 is a fragmentary detail plan view of the agricultural harvesting head of FIG. 2.

In FIG. 3, a left stalk roll 300 and the right stalk roll 302 are mounted for rotation on a row unit gearbox 304. The stalk rolls rotate in opposite directions indicated by the arrow superimposed on the stalk rolls. The stalks of plants are received between the stalk rolls, are engaged by flutes 306 extending from each of the stalk rolls, and are pulled downward.

A left arm 308 and a right arm 310 are fixed to and extend forward from the row unit gearbox 304. The left arm and the right arm support corresponding left side deck plate 312 and right side deck plate 314.

The deck plates 312, 314 are slidably supported on the top surface of the left arm 308 and the right arm 310, respectively, such that the space between them can increase or decrease to allow plant stalks having different diameters to pass between them.

A left side gathering chain 316 and a right side gathering chain 318 extend the length of the left arm 308 and the right arm 310. They are supported on two sprockets disposed on both arms. These sprockets are also driven by the row unit gearbox 304.

The stalk rolls, deck plates and row unit arms define a central gap 116 of generally constant width. Gap 116 extends from the forward end of the deck plates to the row unit gearbox 304. Gap 116 extends fore-and-aft. The plant stalks are guided into gap 116 by the points 112.

Each of the gathering chains has a plurality of protrusions 320 that extend outward and into the gap 113 and the gap 116. These protrusions 320 engage the plant stalks passing into the gaps.

The gathering chains 316, 318 drags the protrusions 320 and the plant stalks rearward, as the stalk rolls pull the plant stalks downward and eject them on the ground.

As the plant stalks are pulled downward, the ears of corn on the plant stalks are pulled against the deck plates 312, 314. This causes the ears of corn to snap off the plant stalks and fall into a space defined between the two adjacent row unit covers 114 and the deck plates 312, 314. As the gathering chains 316, 318 move rearward, they propel the ears of corn in the space backward until the ears fall into the auger trough 107 in which the auger 109 is disposed.

The two row unit covers 114 are disposed on either side of gap 116, just above the gathering chains 316, 318. The two row unit covers 114 have sidewalls 322, 324 that face each other across the gap 116. These sidewalls 322, 324 form fore-and-aft and vertically extending walls of a corn ear collection region 326. The corn ear collection region 326 is bounded at the bottom by the deck plates 312, 314 which prevent ears of corn from falling through the gap 116 and onto the ground. The gathering chains 316, 318 are driven in a direction to convey the ears of corn in the corn ear collection region rearward and into the auger trough 107.

A first sensing element 328 is fixed to sidewall 322 and a second sensing element 330 is fixed to sidewall 324. These sensing elements sense physical characteristics of the ears of corn that have fallen into the corn ear collection region. The sensing elements are elongate and extend longitudinally (i.e. in the fore-and-aft direction "V") along the length of the sidewalls 322, 324. In one arrangement, the sensing elements are conductive wires. In another arrangement, the sensing elements are thin planar sheets of conductive material. These planar sheets may be curved to follow the contours of the sidewalls 322, 324. In one arrangement, the planar sheet is between 1½ and 2½ inches tall (i.e. measured in a vertical direction) and between six and 10 inches long (i.e. measured in the fore-and-aft direction "V". Suitable sensor materials include copper alloys, iron alloys, and aluminum alloys. Sensing elements 328, 330 are preferably embedded within the sidewalls 322, 324, respectively. Alternatively they may be fixed to an inner surface of the sidewalls 322, 324. One method of fixing the sensors to the inner surface of the sidewalls 322, 324 is to first cut a hole 336 in surfaces 332, 334 that are on the opposite side of the row unit covers 114 as the sidewalls 322, 324. The sensing elements are inserted through the hole 336 and into the inner cavity of the hollow body and are fixed to an interior surface of the covers 114. The sensing elements can then be protected from the environment by covering the hole 336 with a cover and thereby sealing the interior of the hollow body.

The row unit arms, the deck plates, the gathering chains, and the first and second sensing elements (328, 330) are disposed vertically in order to place the sensing elements close together and provide a deeper and narrower corn ear collection region 326. Thus, the row unit arms, the deck plates, the gathering chains, and the sensing elements are located underneath each other.

The frequencies of the high-frequency radio signal are selected depending upon the material characteristics of the ears of corn (and more particularly, the kernels on the ears of corn). Frequencies around 5 GHz are well-suited to detect the presence of natural oils within the kernels. These oils are naturally produced as part of the growth process of corn. The amount of natural oils is generally correlated with the volume of corn kernels: the larger the quantity of oil sensed between the sensing elements 328, 330, the greater the volume of grain.

Figure 5:
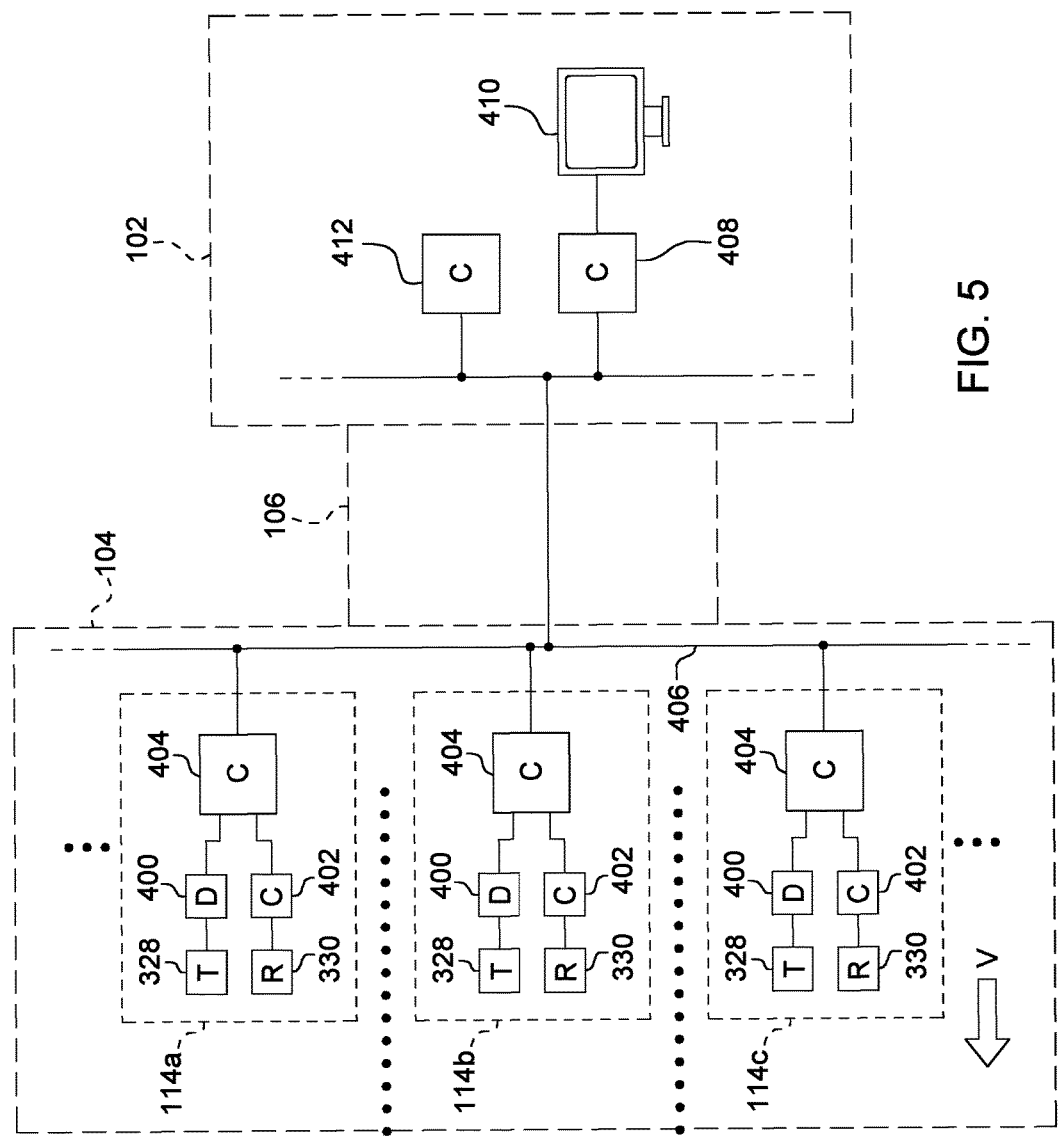
FIG. 5 is a schematic diagram of a yield monitoring system of the agricultural combine of FIGS. 1-4.

FIG. 5 shows a typical arrangement for determining characteristics of the ears of corn (and particularly, the kernels of those ears). FIG. 5 schematically illustrates the agricultural combine 102, the feeder house 106, and the agricultural harvesting head 104 supported on the front of the feeder house 106. Three row unit covers 114 are shown on an agricultural harvesting head 104. While only three covers 114 are shown, the number is arbitrary. As many covers 114 can be provided as row units are mounted on the agricultural harvesting head 104.

Each row unit cover 114 is provided with a first sensing element 328 configured as a transmitter, and second sensing element 330 configured as a receiver. A driver circuit 400 is coupled to the first sensor element to generate the high-frequency radio signal and to apply that signal to the first sensing element 328. The high-frequency radio signal radiates outward from the first sensing element 328, passes through the corn ear collection region 326 and to any ears of corn that have accumulated in this region. The high-frequency radio signal passing through the corn ear collection region 326 is attenuated generally proportional to the quantity of ears of corn in the region 326. The attenuated high-frequency radio signal generates a responsive high-frequency radio signal in the second sensing element 330. This responsive signal is then communicated from the second sensing element 330 to a signal conditioning circuit 402 which is coupled to the second sensing element 330. The signal conditioning circuit 402 filters the responsive signal and communicates the responsive signal to a controller 404. The controller 404 comprises a microprocessor, RAM, ROM, and associated circuitry as well as a CAN bus (SAE J1939) communication circuit. The controller 404 communicates data indicating the magnitude of attenuation of the high-frequency radio signal over a CAN bus 406 to another similarly configured digital microprocessor-based controller 408.

Controller 408 (or alternatively, a similar digital microprocessor-based controller 412) receives the data indicating the magnitude of attenuation of the high-frequency radio signals from the plurality of controllers 404 and calculates a per-acre yield based upon the signals from the magnitudes of attenuation provided by all of the row unit covers 114.

Controller 408 is coupled to a display device 410 to drive the display device 410 and display the per-acre and the per-row yield.

The magnitude of attenuation generally indicates the quantity of ears of corn in the corn ear collection region 326 between two adjacent covers 114. The controller 408 receives signals from each of the controllers 404 associated with a corresponding cover 114 and calculates the yield for each crop row that is harvested. The controller 408 is also configured to combine the individual yields of each row and generate a value indicating the total yield of the entire agricultural harvesting head 104.

In one mode of operation, the driver circuit 400 is configured to drive the first sensing element 328 at frequencies between 1 and 8 GHz. In an alternative mode, it drives them at frequencies between 2 and 6 GHz. In an alternative mode, it drives them at frequencies between 3 and 5 GHz. The signals at these frequencies are preferably sinusoidal waveforms.

Specific frequencies in these ranges are selectively attenuated by different characteristics of the kernels of corn. At driving frequencies around 4 gigahertz, for example, the attenuation is caused by the quantity of oil (i.e. corn oil) contained in the kernels of corn. Since the quantity of oil on a volume basis contained in each corn kernel is relatively constant, the degree of attenuation due to such oil is generally proportional to the volume of corn kernels accumulated in the corn ear collection region 326. It is therefore a good proxy for the volume of corn kernels (i.e. grain) in the corn ear collection region 326. There is little or no corn oil contained in the leaves and cobs of each ear of corn. Therefore, when the high-frequency radio signal is around 4 GHz, the degree of attenuation generally indicates the volume of corn kernels in the corn ear collection region 326.

Figure 4:
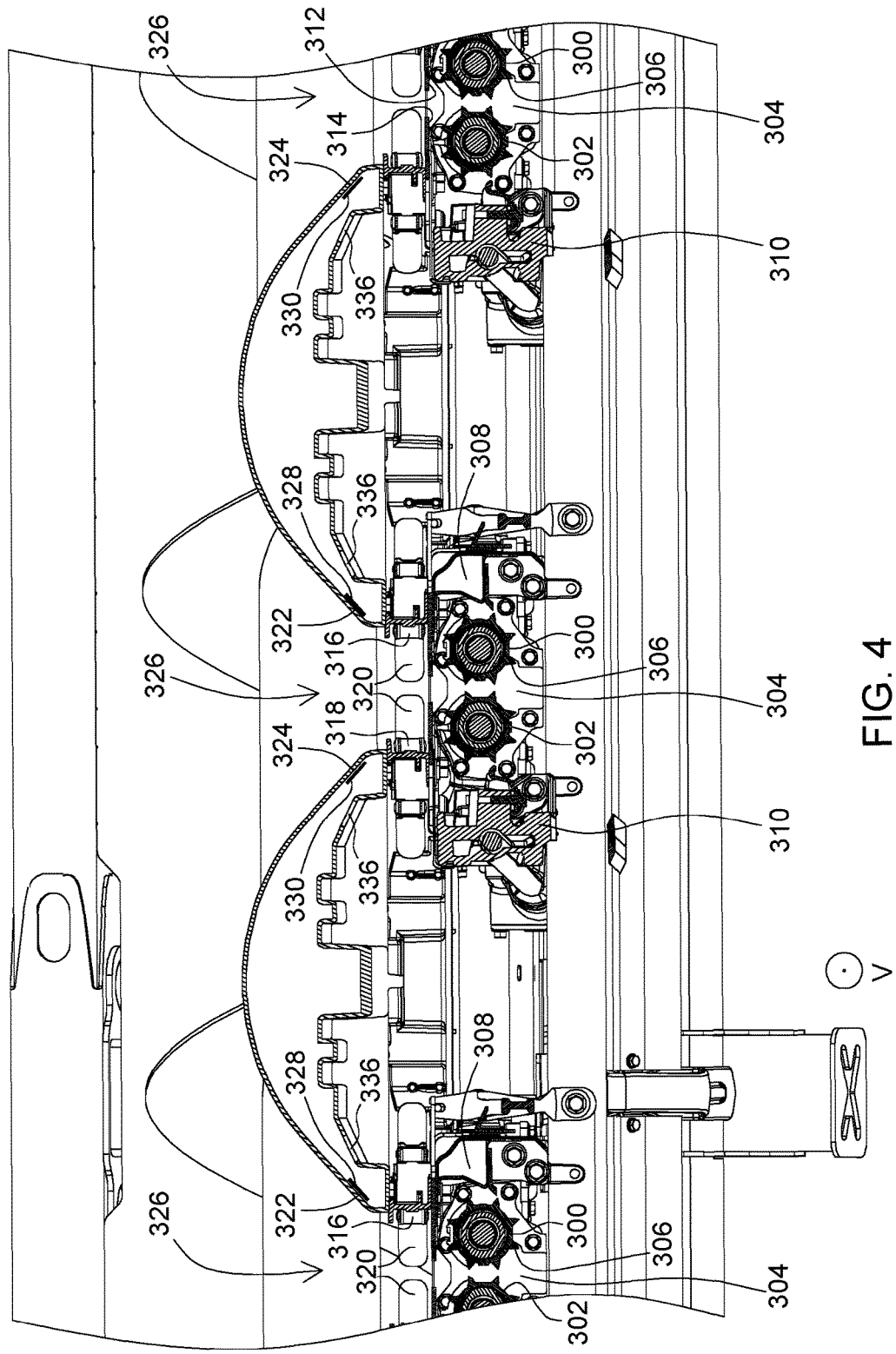
FIG. 4 is a cross-sectional side view of the agricultural harvesting head of FIGS. 1-3 taken at section line 4-4 in FIG. 3.

In another mode of operation, the controller 404 is configured to change the frequency of the high-frequency radio signal emitted by the first sensing element 328 by reconfiguring the driver circuit 400, which in turn generates the high-frequency radio signal at a different frequency. In this manner, other characteristics of the ears of corn can be selectively sensed by the same circuitry associated with each cover 114. In one mode of operation, the controller 404 can be configured to periodically and automatically change the frequency of the high-frequency radio signal by commanding the driver circuit 400 internally reconfigure itself. In this manner, the same sensing arrangement shown in FIG. 4 can be used to sequentially sense a variety of crop characteristics.

It should be noted that the first sensing element 328 that transmits the high-frequency radio signal and the second sensing element 330 that receives the attenuated high-frequency radio signal are not disposed on the same cover 114 in FIG. 5. Instead, the two cooperating sensing elements 328, 330 are disposed on different covers 114 that are adjacent to each other. Thus, the first sensing element 328 on cover 114b transmits a high-frequency radio signal that is received by a second sensing element 328 on cover 114a. Similarly, the first sensing element 328 on cover 114c transmits a high-frequency radio signal that is received by a sensing element 330 on cover 114b. This pattern continues for all of the covers 114 (including those not shown) that extend across the entire width of the agricultural harvesting head 104.

To reduce electrical noise and interference between adjacent row unit covers 114 and to increase the durability of the sensing system, each row unit cover 114 houses a first sensing element 328, a second sensing element 330, a driver circuit 400, a signal conditioning circuit 402, and a controller 404. These individual complements are preferably placed adjacent to each other inside the row unit cover 114. The driver circuit 400, the signal conditioning circuit 402, and the controller 404 are preferably mechanically bonded to one another inside the row unit cover 114.

The claims herein define the invention. The examples described and pictured herein are a few examples of ways to make the invention. Other ways of making the invention are possible.

The invention claimed is:

1. A harvesting head yield monitor for a row unit, wherein the row unit comprises a row unit gearbox, first and second row unit arms coupled to the row unit gearbox and extending forward therefrom, first and second deck plates supported on top of the first and second row unit arms, respectively, and first and second gathering chains disposed on top of the first and second row unit arms, the yield monitor comprising:
   a first row unit cover disposed above the first gathering chain and the first deck plate, wherein the first row unit cover comprises a first hollow plastic body;
   a first sensing element disposed inside the first hollow plastic body immediately above the first gathering chain and the first deck plate;

a driver circuit electrically coupled to the first sensing element and configured to drive the first sensing element to transmit a high frequency radio signal;

a second row unit cover disposed above the second gathering chain and the second deck plate wherein the second row unit cover comprises a second hollow plastic body;

a second sensing element disposed inside the second hollow plastic body immediately above the second gathering chain and the second deck plate, and configured to receive the high-frequency radio signal;

a signal conditioning circuit electrically coupled to the second sensing element and configured to receive the high-frequency radio signal from the second sensing element.

2. The harvesting head yield monitor of claim 1, wherein the driver circuit is disposed inside the first hollow plastic body, and further wherein the signal conditioning circuit is disposed inside the second hollow plastic body.

3. The harvesting head yield monitor of claim 1, further comprising a first digital microprocessor-based controller coupled to the driver circuit and having a CAN bus transceiver, wherein the first digital microprocessor-based controller is disposed within the first hollow body, and further wherein the first digital microprocessor-based controller is configured to control the driver circuit.

4. The harvesting head yield monitor of claim 3, further comprising a second digital microprocessor-based controller coupled to the signal conditioning circuit and having a CAN bus transceiver, wherein the second digital microprocessor-based controller is disposed within the second hollow body, and further wherein the second digital microprocessor controller is configured to receive signals from the signal conditioning circuit.

5. The harvesting head yield monitor of claim 1, wherein the first sensing element and the second sensing element are disposed on opposing lateral sides of a corn ear collection region and further wherein during harvesting operation of the harvesting head an accumulation of ears of corn are interposed between the first sensing element and the second sensing element.

6. The harvesting head yield monitor of claim 5, further comprising:

a first deck plate that is planar and generally horizontal and is disposed at least partially underneath the first row unit cover and extends toward the second row unit cover; and a second deck plate that is planar and generally horizontal and is disposed at least partially underneath the second row unit cover.

7. The harvesting head yield monitor of claim 6, wherein the first deck plate is disposed at least partially underneath the first sensing element, and wherein the second deck plate is disposed at least partially underneath the second sensing element.

8. The harvesting head yield monitor of claim 7, wherein the first gathering chain is disposed at least partially underneath the first sensing element, and wherein the second gathering chain is disposed at least partially underneath the second sensing element.

9. The harvesting head yield monitor of claim 1, wherein the high-frequency radio signal is between 1 and 8 GHz.

10. The harvesting head yield monitor of claim 9, wherein the high-frequency radio signal is between 2 and 6 GHz.

11. The harvesting head yield monitor of claim 10, wherein the high-frequency radio signal is between 3 and 5 GHz.

12. The harvesting head yield monitor of claim 1, wherein the first row unit cover and the second row unit cover are separated by a corn ear collection region and wherein the first sensing element is located just transmit the high-frequency radio signal through the corn ear collection region to the second sensing element such that the high-frequency radio signal passes through ears of corn accumulated in the corn ear collection region.

* * * * *